(12) United States Patent
Urabe et al.

(10) Patent No.: US 6,251,661 B1
(45) Date of Patent: Jun. 26, 2001

(54) SEAMLESS CAPSULE FOR SYNTHESIZING BIOPOLYMER AND METHOD FOR PRODUCING THE SAME

(75) Inventors: Itaru Urabe, Akashi; Tetsuya Yomo, Toyonaka; Keizo Yamamoto, Kitakatsuragi-gun; Hideki Sunohara, Osaka; Ryosei Kamaguchi, Osaka; Yumi Hatano, Osaka, all of (JP)

(73) Assignee: Morishita Jintan Co., Ltd., Osaka-fu (JP)

( * ) Notice: Subject to any disclaimer, the term of this patent is extended or adjusted under 35 U.S.C. 154(b) by 0 days.

(21) Appl. No.: 09/432,823

(22) Filed: Nov. 2, 1999

(51) Int. Cl.$^7$ .............................. C12M 1/34; C12Q 1/68; C07H 21/02
(52) U.S. Cl. .......................... 435/287.2; 435/6; 435/183; 435/91.1; 536/23.1; 536/24.3; 536/24.33
(58) Field of Search ................................ 435/6, 7.1, 91.1, 435/91.2, 183, 69.1; 536/23.1, 24.3, 24.33, 25.3

(56) References Cited

U.S. PATENT DOCUMENTS 5,330,835   7/1994   Kikuchi et al. ................. 428/402.22

FOREIGN PATENT DOCUMENTS 5-31352   2/1993   (JP) .

*Primary Examiner*—Bradley L. Sisson
(74) *Attorney, Agent, or Firm*—Merchant & Gould P.C.

(57) ABSTRACT

This invention provides a seamless capsule for synthesizing biopolymer, comprising:
  (a) an aqueous mixture for synthesizing biopolymer,
  (b) a seamless capsule layer encapsulating said aqueous mixture, formed from polysaccharide or protein, and,
  (c) a viscous liquid intermediate layer, present between said aqueous mixture and said seamless capsule layer, which is immiscible with water,
wherein said seamless capsule has a diameter of 0.01 to 10.0 mm.

This invention can also provide a method for producing the seamless capsule.

23 Claims, 1 Drawing Sheet

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 1
gcgggccacc ccttcaacct c                                                 21

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 2 cagggcacg gcgagggga                                                     19

US 6,251,661 B1

SEAMLESS CAPSULE FOR SYNTHESIZING BIOPOLYMER AND METHOD FOR PRODUCING THE SAME

FIELD OF THE INVENTION

The present invention relates to seamless capsules in which biopolymer can be synthesized, and a production of the seamless capsules.

BACKGROUND OF THE INVENTION

Hitherto, there have been known many techniques for amplifying DNA and RNA and for synthesizing protein. The techniques, for example, include a technique for amplifying DNA fragments of a total volume of 5 to 100 $\mu$L in a plastic reactor, using DNA polymerase as an enzymatic catalyst, or one for synthesizing protein in the. similar volume without an organism.

In the present specification, the amplifying technique performed in a volume of lower than several microliters (e.g. about 5 $\mu$L) is referred to as "reaction in microspace". The amplifying technique called as "reaction in microspace" can complete the reaction in a very small volume and increase its reactivity.

Recently, there has been intensely studied a method for amplifying DNA fragments using enzyme in an artificially created microspace, because it is more effective than the methods conducted through chemical reaction or using organisms The method conducted through chemical reaction has a limit in reactivity and is very difficult to synthesize long DNA fragments. In the case of the amplification using organisms, it is very difficult to synthesize long DNA fragments containing nucleotide analogues because of employing merely nucleic acids naturally oriented. The amplification using organisms also has some problems, for example, the difficulty in screening from the organism to find useful substance. If a conventional small test tube is used as a reactor, it takes a long time to dispense the starting materials into each test tube. In view of the size of the amplifying and screening facilities, the amplification in the test tube needs a large space for reacting and screening.

The method using the artificially created microspace, however, is simple and useful and does not have the above-mentioned problems, in comparison with the methods conducted through chemical reaction or using organisms.

One example of the artificially created microspace is a microcapsule formed from polypyrrole. The polypyrrole capsule is used in the amplification of DNA fragments by encapsulating DNA fragment amplifying components with polypyrrole film using interfacial polymerization. However, the polypyrrole belongs to synthetic polymer and therefore does not have sufficient biocompatibility.

Another method is proposed in which liposome is employed as encapsulating film instead of polypyrrole. Liposome is a bilayer lipid membrane which can be artificially obtained and has similar composition to the cell membrane. It is therefore believed to have high biocompatibility. However, in encapsulating with the liposome, it is difficult to control a size of the capsules. In addition, since the liposome capsules are very soft and fragile, the capsules are easily broken by physical impact given during working, e.g. pinching with a tweezers, and the like.

OBJECT OF THE INVENTION

An object of the present invention is to provide a seamless capsule formed from a novel outer covering material, in order to synthesize or amplify a DNA fragment, a RNA and a peptide, as well as a protein and the like. The seamless capsule can solve the above problems in both the polypyrrole capsule and the liposome capsule.

DEFINITION OF TERMS

Herein, the term "amplification" includes not only amplification of DNA by polymerase chain reaction, that is abbreviated as "PCR", but also includes a transcription of the amplified DNA into RNA and a reverse transcription of RNA into DNA. The term "synthesis" includes the amplification defined above, and a synthesis of protein using the amplified DNA or RNA.

A "cell free protein synthesizing system" means a cell extraction extracted from an organism containing well-known three types of RNA polymerases (i.e. type I, II and III) or the other polymerase, which includes approximately all of components necessary for synthesizing protein.

SUMMARY OF THE INVENTION

The present invention provides a seamless capsule for synthesizing biopolymer, comprising:
  (a) an aqueous mixture for synthesizing biopolymer,
  (b) a seamless capsule layer encapsulating said aqueous mixture, formed from polysaccharide or protein, and,
  (c) a viscous liquid intermediate layer, present between said aqueous mixture and said seamless capsule layer, which is immiscible with water,
wherein said seamless capsule has a diameter of 0.01 to 10.0 mm.

In the present invention, the intermediate layer is formed from a viscous liquid intermediate layer which is immiscible with water and is present between the aqueous mixture for synthesizing biopolymer and the seamless capsule layer by using the technique as described in Japanese Kokai Publication Hei 5 (1993)-31352. The presence of the viscous liquid intermediate layer makes it possible to encapsulate the aqueous mixture for synthesizing biopolymer within the capsule layer.

In more detail, the present invention provides a seamless capsule which comprises the aqueous mixture for synthesizing biopolymer, composed of a template DNA or RNA, primers, substrates and DNA polymerase; the seamless capsule layer; and the intermediate layer. In this seamless capsule, DNA or RNA is amplified by the PCR.

The present invention also provides a seamless capsule which comprises the aqueous mixture for synthesizing biopolymer, composed of a template DNA or RNA, lower molecular components for synthesizing a protein, and a cell free protein synthesizing system; the seamless capsule layer; and the intermediate layer. In this capsule, protein is synthesized.

Furthermore, the present invention provides a seamless capsule which comprises the aqueous mixture for synthesizing biopolymer, composed of a template DNA or RNA, primers, substrates, lower molecular components for synthesizing a protein, DNA polymerase and a cell free protein synthesizing system; the seamless capsule layer; and the intermediate layer. In this capsule, amplification of DNA by the PCR is followed by synthesis of a protein with the amplified DNA.

The present invention can also provide a method for producing a seamless capsule for synthesizing biopolymer therein, comprising simultaneously extruding three different solutions through three nozzles arranged concentrically into a cooling solution, wherein the innermost nozzle extrudes an aqueous mixture for synthesizing biopolymer, the intermediate nozzle extrudes a viscous liquid immiscible with water and the outer nozzle extrudes a capsule layer-forming solution formed from polysaccharide or protein.

The seamless capsule layer of the seamless capsule of the present invention is formed from a polysaccharide, such as curdlan and/or agarose; or a protein. These have good biocompatibility and high light transmittance.

The seamless capsule of the present invention can be formed uniformly by suitably controlling the size of the capsule and the amount of an aqueous mixture during producing The seamless capsule is distinguished from the conventional liposome capsule in good thermostability and high physical strength.

DETAILED DESCRIPTION OF THE PREFERRED EMBODIMENTS

Figure 1:
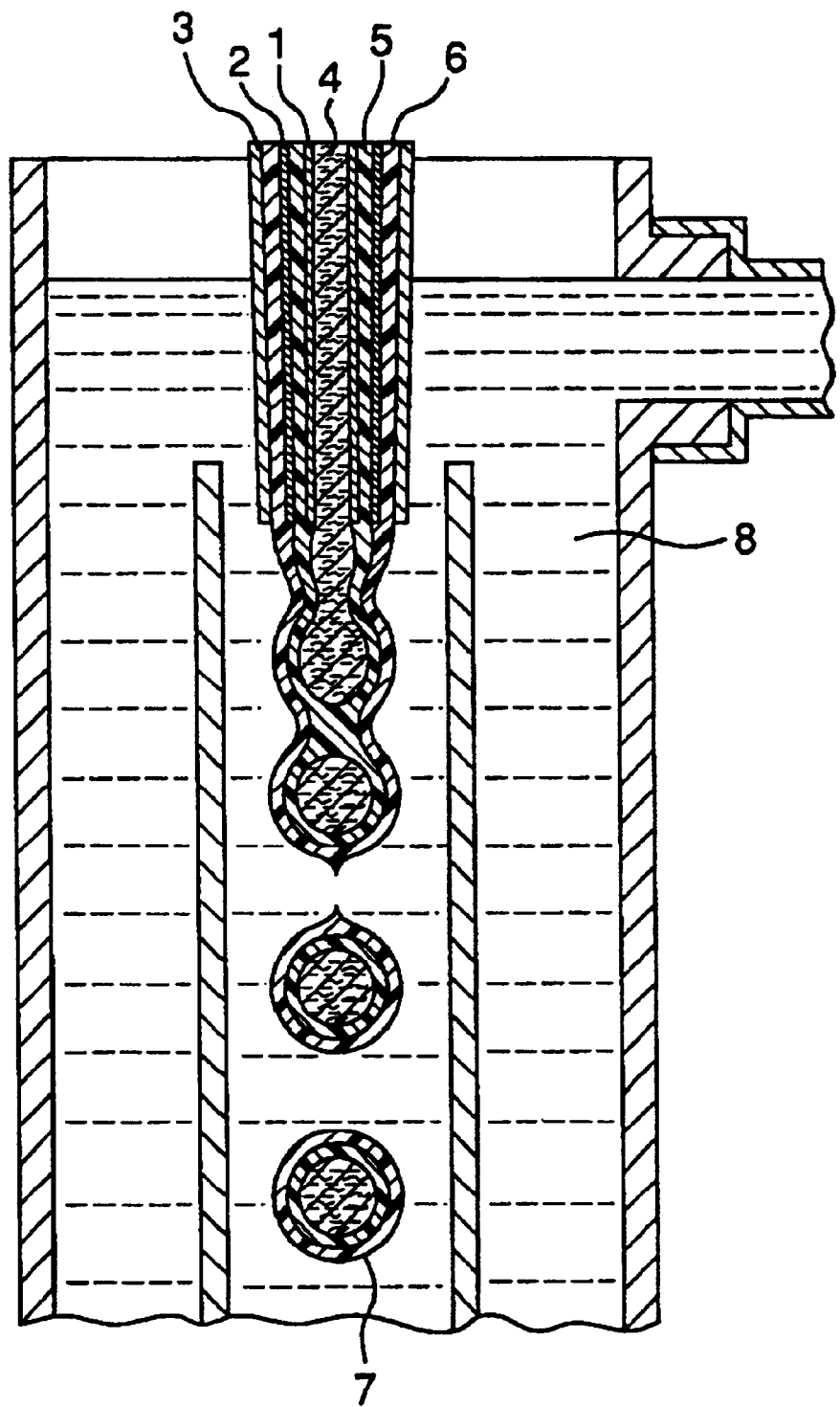
FIG. 1 schematically illustrates a vertical cross sectional view of one embodiment of a suitable apparatus for producing the seamless capsule according to the present invention.

This invention provides a seamless capsule for synthesizing biopolymer, comprising:

(a) an aqueous mixture for synthesizing biopolymer, (b) a seamless capsule layer encapsulating said aqueous mixture, formed from polysaccharide or protein, and, (c) a viscous liquid intermediate layer, present between said aqueous mixture and said seamless capsule layer, which is immiscible with water.

The seamless capsule has a diameter of 0.01 to 10.0 mm.

The seamless capsule layer of the seamless capsule of the present invention may be mainly composed of a polysaccharide or a protein. Examples of the polysaccharide for use in the present invention include curdlan, agarose, guaran gum, pectin, sodium alginate and the like. The protein may be one that is gelled by heating, cooling or adding a bivalent or more-valent metal ion. Specific examples of the protein include gelatin, albumin, casein and the like, but they are not limited thereto The polysaccharide and the protein both have good biocompatibility and high light transmittance, so that they are suitable for forming the seamless capsule layer of the present invention.

Among the components for forming the seamless capsule layer, the polysaccharide or protein may be employed alone or in combination. Alternatively, the polysaccharide or protein can be used together with the other additives, such as gelling agent, water-soluble polyol or water-soluble derivative thereof and the like. Examples of the gelling agent include a bivalent or more-valent metal ion containing compound, for example, calcium chloride, calcium lactate, manganese chloride, aluminum chloride and the like. Examples of water-soluble polyol or water-soluble derivative thereof include glycerin, polyglycerin, sorbitol, ethylene glycol, polyethylene glycol, propylene glycol, polypropylene glycol, ethylene oxide-propylene oxide copolymer, oligosaccharide, sugar ester, glyceride, sorbitan esters and the like.

Preferably, the component for forming the seamless capsule layer of the seamless capsule of the present invention can be curdlan or agarose or a mixture thereof. More preferably, a mixture of curdlan and agarose in a weight ratio of 1:1 is employed, because among the mixture contained in the seamless capsule, a component having a molecular weight of lower than 700 can permeate through the seamless capsule layer of the capsule. The permeability can be controlled depending on the material used for the viscous liquid intermediate layer.

In forming the seamless capsule layer, the polysaccharide or protein may preferably be contained in an amount of 50 to 100 percent by weight based on the total of the solid content. The gelling agent, water-soluble polyol or water-soluble derivative thereof may be contained in an amount of 1 to 50 percent by weight based on the polysaccharide.

A viscous liquid which is immiscible with water may desirably have a viscosity of lower than 1,000 centipoise in view of the formation of a uniform thin film as the intermediate layer. The viscous liquid generally includes an emulsifier, an oil or a resin. The emulsifier suitably used for the viscous liquid in the seamless capsule of the present invention may be a nonionic emulsifier having a HLB value of 2 to 8, for example sucrose fatty acid ester, propylene glycol fatty acid ester, glycerin fatty acid ester (e.g. long chain fatty acid triglyceride, middle-length chain fatty acid triglyceride, etc.), sorbitan fatty acid ester; and an amphotelic ionic emulsifier such as lecithin; or a mixture thereof. The oil may include a plant oil, an animal oil and a mineral oil, for example, palm oil, silicone oil, liquid paraffin or a mixture thereof. The resin used for the viscous liquid includes dl-α-tocopherol, isobutylene polymer (such as polybutylene or polybuten), silicone resin, vinyl acetate, and the like.

The viscous liquid intermediate layer in the seamless capsule according to the present invention may preferably be formed from a mixture of the emulsifier and the oil, more preferably, a mixture of sucrose fatty acid ester and palm hydrogenated oil in a weight ratio of 1 to 4: 4 to 1, most preferably 4:1.

In the seamless capsule of the present invention, the viscous liquid as mentioned above, exists in the form of the intermediate layer between the aqueous mixture (a) and the seamless capsule layer (b), when producing the capsule. However, the viscous liquid, after production, may not exist between the aqueous mixture (a) and the seamless capsule layer (b) and can be present as separated material within the capsule.

In the first embodiment of the present invention, the aqueous mixture for synthesizing biopolymer (a) is a mixture of a template DNA or MA, primers, substrates and DNA polymerase. Amplification of DNA by the PCR and transcription of the amplified DNA to RNA can be performed in the seamless capsule of the first embodiment of the present invention.

The seamless capsule layer and the viscous liquid can be selected from the above mentioned materials.

Examples of the nucleic acid template encapsulated in the seamless capsule of the first embodiment include DNA and messenger RNA both extracted from an organism, an artificially synthesized DNA or RNA, etc. Base components contained in the DNA extracted from an organism may be adenine, cytosine, guanine and thymine. Base components contained in the RNA extracted from an organism may be adenine, cytosine, guanine and uracil. The artificially synthesized nucleic acid can contain base components other than the above mentioned one, as long as DNA polymerase can use them as substrates.

The component for synthesizing the biopolymer in the seamless capsule of the present invention may be composed of primers and substrates.

Herein, the primer means a single strand of DNA fragment composed of about 10 to about 50 bases, such as natural or unnatural oligonucleotide. The primer can be an essential element for amplifying DNA by the PCR and also needs to define a starting point of synthesis by DNA polymerase. The starting point of synthesis can be selected arbitrarily. The primer can be one which is subjected to reaction by the recognition of the DNA polymerase contained in the capsule, and has a complementary sequence to the template DNA or RNA.

The substrate used for the first embodiment of the present invention can be an essential element for synthesizing DNA by the PCR in the seamless capsule. Therefore, in case of amplification of DNA in the capsule, the substrate may be composed of four mono-nucleotides (i.e. deoxyadenosine 5'-triphosphate, deoxycytidine 5'-triphosphate, deoxyguanosine 5'-triphosphate and deoxythymidine 5'-triphosphate; these four mono-nucleotides are inclusively called "dNTPs") comprising the base components (i.e. adenine, cytosine, guanine and thymine), and sugar (i.e. 2-deoxy-D-ribose). The substrate may further contain deoxyinosine 5'-triphosphate.

In the seamless capsule of the first embodiment of the present invention, the substrate which needs to synthesize RNA may be composed of four mono-nucleotides comprising the base components (i.e. adenine, cytosine, guanine and uracil) and sugar (i.e. ribose).

When amplifying the DNA fragment from the template DNA by the PCR in the seamless capsule, DNA polymerase should be contained therein. When synthesizing complementary-DNA, i.e. cDNA, from the template RNA in the seamless capsule, a reverse transcriptase or DNA polymerase acting as a reverse transcriptase should be contained together with DNA polymerase in the capsule. In case of synthesis of cDNA, the capsule may be warmed at a temperature that the reverse transcriptase can be active for a given period to synthesize a cDNA, and then, if necessary, the PCR may be performed to amplify the cDNA.

In the seamless capsule of the first embodiment of the present invention, RNA polymerase can be contained so as to transcribe the synthesized DNA or cDNA to form a desirable RNA.

Accordingly, the capsule of the first embodiment of the present invention may contain one or more polymerases necessary to produce a desirable DNA or RNA.

In the first embodiment of the present invention, the seamless capsule may preferably contain one to $1 \times 10^{10}$ molecules of the template DNA or RNA, 10 to 100 picomoles of the primers, 0.1 to 0.4 mM of the substrate and 0.1 to 4 U of the polymerase, based on 100 $\mu L$ of the total aqueous mixture for synthesizing biopolymer (a). In the present invention, 1 U of a polymerase defines as an amount of oxygen necessary for incorporating 10 nanomoles of dNTPs into an acid-insoluble precipitate for 30 minutes, when M13mp18 ss DNA and the primers thereof are employed as the substrates under a condition which can determine an activity of the polymerase at a temperature 75° C.

Thereafter, the DNA or the RNA obtained in the seamless capsule of the first embodiment of the present invention can be extracted from the capsule by art-known method, such as centrifugation technique, suction technique with a capillary, and the like.

In the above capsule, the DNA or the RNA can be obtained in an amount corresponding to about 0.1 to 20 KB.

In the second embodiment according to the present invention, the aqueous mixture for synthesizing bitpolymer (a) contains a template DNA or RNA, lower molecular components for synthesizing a protein and a cell free protein synthesizing system. In the seamless capsule, a desirable protein can be synthesized with the lower molecular components for synthesizing a protein, which includes amino acids, etc., and the cell free protein synthesizing system from the template DNA or RNA.

The seamless capsule layer and the viscous liquid can be selected from the above mentioned materials.

The template DNA or RNA contained in the capsule of the second embodiment of the present invention may be any one that previously described in the capsule of the first embodiment. The DNA amplified in the seamless capsule of the first embodiment or the RNA synthesized from the DNA can be used as the template. In the latter, the DNA or the RNA obtained in the capsule of the first embodiment of the present invention may be encapsulated in the capsule of the second embodiment in the form which enclosed in the capsule of the first embodiment, as it is, or in the form of an extract extracted from the capsule of the first embodiment by the method described hereinbefore.

In the seamless capsule of the second embodiment of the present invention, the "cell free protein synthesizing system" means a cell extract extracted from an organism, which intends to include approximately all of elements necessary for synthesizing a protein, containing art-known three types of RNA polymerases (i.e. type I, II and III) or the other polymerase. Examples of the cell free protein synthesizing system may be a known mixture, such as S-30 fraction or S-100 fraction. Particularly, the S-30 fraction is believed to contain a ribosome, a RNA polymerase, aminoacyl tRNA synthetase and the like, but all of components thereof has not been identified yet. The S-30 is explained in detail in Translation and Transcription, section seven, Julie M. Pratt, "Coupled Transcription—Translation in Prokaryotic Cell Free Systems", IRL Press Oxford, 1984. In the present invention, if all of the components are identified, the components contained therein can be separately obtained and then mixed together to use as the cell free protein synthesizing system.

The cell free protein synthesizing system may be employed alone or in combination. According to a protein to be synthesized, a ribosome may be isolated from the a cell free protein synthesizing system by a known release reaction to be employed together with the other cell free protein synthesizing system.

The lower molecular components for synthesizing a protein contained in the second embodiment of the present invention may be served as a mixture containing elements necessary for inducing a reaction to be added into the cell free protein synthesizing system, for example amino acids, ATP, GTP, tRNA, an energy-regenerating system, a synthetic mRNA and magnesium ion, potassium ion or ammonium ion in an adequate amount, and the like. In the context, the amino acids include 20 types of amino acids consisting of glycine, alanine, valine, leucine, isoleucine, serine, threonine, aspartic acid, glutamic acid, asparagine, glutamine, lysine, arginine, cysteine, methionine, phenylalanine, tyrosine, tryptophan, histidine and proline.

In this second embodiment, the aqueous mixture for synthesizing biopolymer (a) in the seamless capsule may preferably contain 7 to 14 $\mu g$ of the template DNA or RNA, 25 to 50 $\mu L$ of the lower molecular component for synthesizing a protein and 30 $\mu L$ of the cell free protein synthesizing system, based on 100 $\mu L$ of all of the aqueous mixture for synthesizing biopolymer.

Then, the protein synthesized in the seamless capsule can be extracted and isolated from the capsule by an art-known method, such as centrifugation technique, suction technique with a capillary and the like.

In the capsule of the second embodiment, a protein such as luciferase, phosphatase, DNA polymerase, etc. can be synthesized. When the synthesized DNA polymerase may be used to perform the PCR again, a template DNA can also be amplified.

In the third embodiment of the present invention, the aqueous mixture for synthesizing biopolymer (a) contains a template DNA or RNA, primers, substrates, lower molecular components for synthesizing a protein, DNA polymerase and a cell free protein synthesizing system.

In the seamless capsule of the third embodiment, an adequate DNA can be amplified with the template DNA or RNA by the PCR, and then the amplified DNA is employed for synthesizing a desirable protein via a transcription of the DNA to a mRNA.

The seamless capsule layer, the viscous liquid and the template DNA or RNA enclosed in the capsule can be selected from the above mentioned materials.

In the seamless capsule of this third embodiment, the aqueous mixture for synthesizing biopolymer comprises primers and substrates.

The primer may be any one selected from the same component as previously described in the first embodiment. As the template DNA, the seamless capsule of the third embodiment can also contain the DNA synthesized or amplified in the capsule of the first embodiment in the form of capsules, as it is, or in the form of an extract which has been extracted by the method described above.

The substrates include four types of monodeoxynucleotides for synthesizing DNA, i.e. dNTPs, four types of mononucleotides for synthesizing RNA and mononucleotide such as deoxyinosine 5'-triphosphate and the like, as described above in this first embodiment. The use of the mononucleotides for synthesizing RNA is particularly important, depending on the kind of protein to be synthesized.

The cell free protein synthesizing system, the lower molecular components for synthesizing a protein and the polymerase which needs to obtain a desirable nucleic acid may be the same as described in the second embodiment.

Alternatively, the cell free protein synthesizing system may be employed alone or in combination. Depending on the type of protein to be synthesized, a ribosome can be isolated from the cell free protein synthesizing system by a well known release reaction, and then, used in combination with the other cell free protein synthesizing system.

In the seamless capsule of the third embodiment, the aqueous mixture for synthesizing biopolymer (a) may preferably contain 1 to $1 \times 10^{10}$ molecules of the template DNA or RNA, 10 to 100 picomoles of each primer, 0.1 to 0.4 mM of all of the substrates, 25 to 50 μL of the lower molecular components for synthesizing a protein, 0.1 to 4 U of the polymerase and 30 μL of the cell free protein synthesizing system, based on 100 μL of all of the aqueous mixture for synthesizing biopolymer.

The protein synthesized in the seamless capsule can be extracted and isolated from the capsule by an art-known methods such as centrifugation technique, suction technique with a capillary and the like.

In the seamless capsule of the third embodiment, protein, e.g. luciferase, phosphatase, DNA polymerase, etc. can be synthesized.

Another embodiment of the present invention provides a method for producing the above mentioned seamless capsule. This method will be explained in detail according to an accompanying drawing.

FIG. 1 schematically illustrates a vertical cross sectional view of a nozzle portion of an apparatus suitable for producing a seamless capsule according to the present invention.

The nozzle in the apparatus used for the method of the present invention is generally formed from a resin or a metal ,and the like, which does not adversely effect on the aqueous mixture for synthesizing biopolymer (a), but preferable examples are silicone resin, teflon resin, i.e. polytetrafluoroethylene, stainless steel, titanium, ceramics or a combination thereof.

As shown in FIG. 1, a seamless capsule (7) of the present invention can be produced by concurrently extruding an aqueous mixture for synthesizing biopolymer of the capsule (4) through an inner nozzle (the first nozzle) (1), the viscous liquid which is immiscible with water (5) through an intermediate nozzle (the second nozzle) (2) and the seamless capsule layer forming component (6) through an outer nozzle (the third nozzle) (3), respectively, to make a three-phase jet stream, followed by releasing the jet stream into a cooling solution (8).

In the method for producing the capsule, since all of the loading materials are all liquid, the encapsulation process can be easily performed by adequately vibrating the jet stream with a vibration means. A particle size of the resulting capsules may be controlled uniformly and formed into a desirable size of 0.01 to 10.0 mm in diameter depending on its application.

The seamless capsule produced by the above method may be employed with or without drying.

In the method for synthesizing biopolymer in the seamless capsule of the present invention, components suitable for a target biopolymer are encapsulated into a capsule, and then, the capsule is warmed for a sufficient period at a temperature which the polymerase or cell extract, i.e. cell free protein synthesizing system, starts reaction. During the reaction, if necessary, conditions surrounding the capsules can be changed to adjust type of low molecular components or pH value in the capsule using the permeability of the seamless capsule layer.

The DNA, RNA or biopolymer such as protein and the like synthesized in the capsule can be identified by well-known technique, e.g. electrophoresis, high performance liquid chromatography, enzyme immunoassay, etc.

The seamless capsule of the present invention has the following advantages.

(1) The seamless capsule of the present invention can provide a microspace for synthesis. In the microspace, one strand of the template DNA or RNA can be encapsulated in each seamless capsule by lowering a concentration of the template DNA or RNA based on all elements contained in the capsule. On the other hand, when a mixture of various types of the templates is encapsulated and reacted, then the capsule contains many types of the resulting product as a library. Since the seamless capsule of the present invention has uniform particle size, high physical intensity and light transmittance, it may be possible to automatically screen useful products from the library, which results in high productivity.

(2) Since the reaction of the template DNA or RNA is performed inside the artificially created seamless capsule, artificially synthesized material other than biosynthesized material, such as toxic material (against organism), can be produced.

(3) The size of the capsule and the amount of ingredients encapsulated therein can be freely varied, so that the amount of a product can be controlled corresponding to a detective range of a detecting apparatus. Accordingly, the present invention makes it possible to produce a given material which has not been detected before.

(4) The seamless capsule of the present invention has a good biocompatibility, so that it may be administered to an organism without extracting the product therefrom.

In the seamless capsule of the present invention, a desirable biopolymer can be easily and quickly synthesized, and therefore, the problems associated with the synthesis or amplification in the liposome or polypyrrole capsule have been obviated.

EXAMPLES

The following Examples further illustrate the present invention in detail but are not to be construed to limit the scope thereof to their details.

Example 1

PCR (Polimerase Chain Reaction) in a Seamless Capsule

1) Preparation of an aqueous mixture and a solution used for forming a seamless capsule A template DNA, tricine-NaOH, β-mercaptoethanol, magnesium chloride, dNTPs, primers and a Tth polymerase as an aqueous mixture of a seamless capsule were mixed in the amounts as shown below, to which sterile water was added, to obtain an aqueous mixture having a given concentration.

Formulation of the aqueous mixture:

| template DNA[+)] | $1 \times 10^8$ molecules based on 100 μL of all of the formulation |
|---|---|
| Tricine-NaOH (pH = 8.3) | 30 mM |
| β-mercaptoethanol | 5 mM |
| Magnesium chloride | 1 mM |
| dNTPs | every 0.2 mM |
| Primer[++)] | every 100 picomoles based on 100 μL of all of the formation |
| Tth polymerase[+++)] | 2 U based on 100 μL of all of the formation |

[+)]: The template DNA was obtained by using a gene of DNA polymerase I derived from Thermus thermophilus, where in 0.9 KB of inside thereof were synthesized.
[++)]: The following two base sequences were used as a primer;
Primer C10: GCGGGCCACCCCTTCAACCTC [SEQ ID NO: 1]
Primer D2: CAGGGGCACGGCGAGGGGA [SEQ ID NO: 2]
[+++)]: DNA polymerase I derived from Thermus thermophilus HB8, commercially available from TOYOBO CO., LTD.

+): The template DNA was obtained by using a gene of DNA polymerase I derived from *Thermus thermophilus*, wherein 0.9 KB of inside thereof were synthesized.

++): The following two base sequences were used as a primer;
Primer C10:
  GCGGGCCACCCCTTCAACCTC [SEQ ID NO: 1]
Primer D2:
  CAGGGGCACGGCGAGGGGA [SEQ ID NO: 2]

+++) DNA polymerase I derived from *Thermus thermophilus* HB8, commercially available from TOYOBO CO., LTD.

A solution for forming seamless capsule layer of the seamless capsule was prepared by mixing curdlan having a number average molecular weight of 500 to 5,000, preferably 1,000 to 3,000, and agarose having of about $1 \times 10^6$. A solution for forming intermediate layer arranged between the seamless capsule layer and the aqueous mixture of the capsule was prepared by mixing palm hardened oil and sucrose fatty acid ester (SAIB).

2) Production of a capsule

The aqueous mixture and the solutions for forming intermediate layer and seamless capsule layer were charged into an apparatus for forming a seamless capsule manufactured by MORISITA JINTAN CO., LTD., respectively.

| Formulation | percent by weight |
|---|---|
| The aqueous mixture | 10 |
| The intermediate layer | |
| Palm hardened oil | 24 |
| Sucrose fatty acid ester | 6 |
| The seamless capsule layer | |
| Curdlan | 0.6 |
| Agarose | 0.6 |
| Aqua purifcata | 58.8 |
| | 100.0 |

In the apparatus, a temperature and a flow rate for the aqueous mixture were adjusted to 25 and 4.9 mL/minute; for the solution for forming intermediate layer were 60° C. and 16.4 mL/minute; and for the solution for forming seamless capsule layer were 60° C. and 29.6 mL/minute. The three-phase jet stream consisting of the aqueous mixture and the solution for forming intermediate layer and the solution for forming seamless capsule layer were concurrently extruded into a cooling solution at 8° C. and at a flow rate of 938 mL/minute to obtain seamless capsules having a size of 3.0 mm in diameter.

3) PCR

One capsule obtained by the above method was put into a 0.6 mL reaction tube which was made of polypropylene, and then, a mineral oil which, commercially available from Sigma Co., LTD., added thereto so as to perfectly soak the capsule in the oil. The reaction tube was equipped to Thermal Cycler PC700 manufactured by ASTECH CO., LTD. to perform the PCR according to the PCR program of the following step (i), (ii) and (iii).

PCR Program

Step (i); at 94° C. and for five minutes, which was performed one cycle,

Step (ii); at 94° C. and for one minute, at 54° C. and for one minute and at 72° C. and for five minutes: which were repeated 40 cycles, and Step (iii); at 72° C. and for ten minutes: which performed one cycle.

4) Extraction of the product

After the PCR, the capsule was transferred from the reaction tube to an Eppendorf tube equipped with a 0.22 μm filter to centrifuge at a rotation rate of 5,000×g for 20 minutes, and then, the content in the capsule was collected. The content was concentrated to at least ten times by means of the Ultrafree C3-LTK ultrafilter which cut a lower molecular weight of less than 30,000, commercially available from Millipore Corporation.

5) Quantification of the synthesized DNA

To 10 μL of the above concentrate, 2 μL of 6×Dye (the dye composition containing 0.25 % by weight of bromophenol blue, 0.25 % by weight of xylenesyanol and 15 % by weight of Ficoll (Type 400 pharmacia)) was added and electrophoresed on a well of 1.0 % agarose gel. As a control, a DNA of which a length and a concentration were previously known was concurrently electrophoresed. After electrophoresis, the gel was stained with ethydium bromide, irradiated to a ultraviolet light. A quantum of the color developed DNA was determined by comparing with the control. At a result, 0.1 to 2.0 μg of DNA was confirmed to be synthesized, based on 10 μL of the content. The quantum of the synthesized DNA was about 0.9 kB.

Example 2

Synthesis of Protein in the Capsule

At first, a cell free protein synthesizing system derived from *Escheritia coli*, that was called as "*E. coli* S-30 fraction" hereinafter, was prepared according to the following procedure.

Strain: *Escheritia coli* DPB267, that was called as *E. coli* DPB267 hereinafter.

| a) 2xTY plate culture media (an amount per one litter of all of the reactant) | |
|---|---|
| Tryptone (a nitrogen source, commercially available as a trade name of "Bacto-Tryptone" from Difco CO., LTD.) | 16 g |
| Yeast extract (commercially available as a trade name of "Yeast Extract" from Difco CO., LTD.) | 10 g |
| Sodium chrolide | 5 g |
| b) A culture media for preparing S-30 fraction | |
| Solution I: a mixture of 56 g of $KH_2PO_4$, of $K_2HPO_4$ and 10 g of the yeast extract. | 289 g |
| Solution II: 25% (W/V) of glucose | 800 mL |
| Solution III: 0.1 M magnesium acetate | 100 mL |
| Thiamine | 15 mg |
| Methionine | 0.5 g |

These solution I, II and III were independently subjected to sterilization with an autoclave. Thiamin and methionine were subjected to sterilization with a 0.22 μm filter before use. After sterilization, all of these components were mixed together.

| c) Buffering solution for S-30 fraction I | |
|---|---|
| Tris-acetate (pH 8.2) | 10 mM |
| Magnesium acetate | 14 mM |
| Potassium acetate | 60 mM |
| DTT | 1 mM |
| d) Buffering solution for S-30 fraction II | |
| Tris-acetate (pH 8.2) | 10 mM |
| Magnesium acetate | 14 mM |
| Potassium acetate | 60 mM |
| DTT | 1 mM |
| 2-mercaptoethanol | 50 μL/L |
| e) Preliminary mixture | |
| ATP (pH 7.0) | 13.2 mM |
| Tris-acetate (pH 8.2) | 0.3 M |
| Phosphoenolpyruvate | 84 mM |
| Magnesium acetate | 9.2 mM |
| DTT | 4.4 mM |
| 19 types of amino acids (glycine, alanine, valine, leucine, isoleucine, serine, threonine, aspartic acid, glutamic acid, asparagine, glutamine, lysine, arginine, cysteine, phenylalanine, tyrosine, tryptophan, histidine and proline) | every 0.04 mM |
| Methionine | 1 mg/mL |
| Pyruvate kinase | 7 U/mL |
| 1% (v/v) of ADEKANOL (an alcoholic defoaming agent, commerically available from ASANI DENKA KOGYO K.K.) | 1.5 mL |

*E. coli* was coated on the 2xTY plate culture media and incubated at a temperature of 37° C. for twelve hours(a). Then, one platinum loop of bacterial strain was inoculated to the 5 mL 2xTY culture media (a) and cultivated at a temperature of 37° C. for twelve hours with shaking (: preliminary primary incubation). Two milliliters of the preliminary primary incubated culture was inoculated to 200 mL of the culture media for preparing S-30 fraction (b) and cultivated at a temperature of 37° C. for twelve hours with shaking (: primary incubation). All of the primary incubated culture was inoculated to 6 liters of the culture media for preparing S-30 fraction (b) and cultivated at a temperature of 37° C. in a jar fermenter which was settled at 3.5 vvm of an oxygen flow rate and at a rotation rate of 800 rpm. Then, 1.5 mL of Adekanol as a deforming agent was added to the culture. During incubating, for the culture, an optical density ($OD_{450}$) at 450 nm was measured with time. Before $OD_{450}$ reached to 2.0, the culture was cooled and collected. The collected cell pellet was washed with the cooled buffering solution for S-30 fraction I (c), and then, maintained at −80° C. through a night.

After that, the cell pellet was defrosted on ice. The ice-cooled buffering solution for S-30 fraction II (d) was further added thereto, and then, collected again.

12.7 Milliliters of the ice-cooled buffering solution for S-30 fraction I (c) based on 10 g of the cell pellet was added and suspended until the solution was sufficiently uniform. The cell pellet contained in the solution was disrupted with a Frenchpress at 8400 PSI manufactured by SLM Instruments, Inc.

100 Microliters of DTT per 10 mL of the disrupted cell lysate was added, centrifuged at a temperature of 4° C. for 30 minutes, at a rotation rate of 30,000×g, and then, a supernatant was separated. Three mL of the preliminary mixture (e) per 10 mL of the supernatant was added to the supernatant, and the mixture was mildly shaken at 37° C. for 80 minutes. The mixture was introduced into a dialysis membrane to be dialyzed with 500 mL of the buffering solution for S-30 fraction I (c) at a temperature of 4° C. for two hours. During dialysis, the outer (dialysis) solution was changed every 30 minutes. After that, the mixture was centrifuged at 4° C. for 5 minutes at a rotation rate of 2,000×g. A supernatant obtained by centrifugation was called as S-30 fraction. After preparation, S-30 fraction was divided every 2 mL to keep it in a liquid nitrogen. This was employed as *E. coli* S-30 fraction hereinafter.

1) Formation of an aqueous mixture for capsules

A template DNA:

A promoter and a SD sequence recognized by *E. coli* was incorporated into a head of a luciferase gene derived from a fire fly, and then, the total length thereof was synthesized by the PCR to employ.

*E. coli* S-30 fraction

A mixture of lower molecular components for synthesizing a protein (LM mixture).

| | |
|---|---|
| Magnesium acetate | 74 mM |
| Ammonium acetate | 144 mM |
| Potassium acetate | 288 mM |
| Dithiothreitol (DTT) | 7 mM |

-continued

| Isopropylthiogalactopyranoside (IPTG) | 2 mM |
| --- | --- |
| 5',3'- cAMP sodium salt | 2.6 mM |
| tRNA derived from MRE600 | 0.68 mg/mL |
| Phosphoenol pyruvate monopotassium salt | 108 mM |
| Calcium folate | 134.9 mg/mL |
| Polyethylene glycol 8000 | 7.6% |
| ATP | 4.9 mM |
| GTP | 3.4 mM |
| CTP | 3.4 mM |
| UTP | 3.4 mM |
| 20 types of amino acids (glycine, alanine, valine, leucine, isoleucine, serine, threonine, aspartic acid, glutamic acid, asparagine, glutamine, lysine, arginine, cysteine, methionine, phenylalanine, tyrosine, tryptophan, histidine and proline) | every 1.3 mM |

2) Production of capsules

The *E. coli* S-30 fraction was taken out from the liquid nitrogen and defrosted on ice with shading form light. The aqueous mixture was prepared by mixing the components of the aqueous mixture of the capsule in the composition as shown bellow.

Composition for an aqueous mixture (per one milliliter of the total content solution);

| A template DNA | 70 µg |
| --- | --- |
| The *E. coli* S-30 fraction | 0.3 mL |
| LM mixture | 0.25 mL |
| sterile water | to be 1 mL in all |

Example 1 was repeated to prepare a seamless capsule, with the exception that the aqueous mixture containing the above composition was employed.

One capsule obtained by the above method was introduced into a 0.6 mL reaction tube which was made of polypropylene, and then, a mineral oil, commercially available from Sigma CO., LTD., added thereto so as to perfectly soak the capsule in the oil. The reaction tube was fixed to Thermal Cycler PC700 manufactured by ASTECH CO., LTD. to perform the PCR at a temperature of 37° C. for two hours.

3) Extraction of the product

After the reaction, the capsule was transferred from the reaction tube to a centrifuge filter with a 0.22 µm membrane filter to centrifuge at a rotation rate of 5,000×g for 20 minutes. Then, the content solution was collected.

4) Detection of activity of luciferase

Detection was performed according to a protocol of new reporter gene luciferase assay system picker gene kit manufactured by TOYO INK CO., LTD. Ten microliters of the capsule extract was added to the kit based on 50 µL of an illuminating substrate contained therein to agitate. Immediately, emission was measured with a E. G. & G. BERTHOL Lumat LB9501 type luminometer for 30 minutes to detect activity of the synthesized luciferase. As a control, a standard curve was determined by using a commercial reagent of luciferase. As a result, it has been found that luciferase was synthesized in an amount of 10 to 100 femtomoles based on 10 µL of the capsule extract.

Example 3
Synthesis of a Protein in a Capsule by the PCR

1) Composition

An aqueous mixture for a capsule was prepared by mixing the following components and diluted with sterile water.

Composition for an aqueous mixture:

| A template DNA[+) | $1 \times 10^9$ molecules based on 100 µL of all of the formation |
| --- | --- |
| Tricine-NaOH (pH = 8.3) | 300 mM |
| β-mercaptoethanol | 50 mM |
| Magnesium chloride | 10 mM |

[+) These configuration were previously shown in Example 1.

(These three components were combined together to be 10 microlitters in all.)

| dNTPs (A mixture of four types of NTP's in an amount of every 2 mM). | 10 µL |
| --- | --- |
| Primer C10 and D2 | every 100 picomole based on 100 µL of all of the formation |
| Tth polymerase[++) | 2 U based on 100 µL of all of the formation |
| *E. coli* S-30 fraction[+++) | 30 µL |
| LM mixture[++++) | 22.5 µL |
| sterile water | to be 100 µL in all |

++): DNA polymerase I derivated from *Thermus thermophilus* HB8 which is commercially available from TOYOBO CO., LTD.

+++): Prepared according to Example 2 with the exception that *thermus thermophillus* HB8 was used as a strain, and that a incubation temperature was settled at 65° C.

++++): It was one which magnesium acetate was removed from LM mixture of Example 2.)

Example 1 was repeated to prepare a seamless capsule with the exception that the aqueous mixture containing the above compositions was employed.

2) PCR (polymerase chain reaction)

The capsule obtained above was dialyzed for 30 mM of Tricine-NaOH (pH 8.3) at a temperature of 4° C. through a night. Then, the capsule was subjected to the PCR on Thermal Cycler PC700, manufactured by ASTECH CO., LTD., according to the following PCR program, which comprises the step (i) and (ii), PCR program Step (i); at 94° C. and for 60 seconds, which was performed one cycle, and Step (ii); at 94° C. and for 30 seconds and at 68° C. and for four minutes, which were repeated 35 cycles.

After the PCR, the capsule was dialyzed for the LM mixture at a temperature of 4° C. for 6 hours. Sequentially, the capsule was further reacted at a temperature of 68° C. for two hours to synthesize protein.

4) Extraction of the product

After the PCR, the capsule was transferred from the reaction tube to an Eppendorf tube equipped with a 0.22 µm filter to centrifuge at a rotation rate of 5,000×g for 20 minutes, and then, the content in the capsule was collected. The content was concentrated to at least ten times by means of the Ultrafree C3-LTK ultrafilter which cut a lower molecular weight of less than 30,000, commercially available from Millipore Corporation.

5) Detection of activity of alkaline phosphatase

Ten microliters of the capsule concentrate and 50 µL of an illuminating substrate of alkaline phosphatase (that is named CSPD™; manufactured by TROPIX INC.) were charged into a micro assay plate with 96 holes and combined together to detect activity of alkaline phosphatase. As a control, a diluted commercial reagent of alkaline phosphatase was mixed with the illuminating substrate in the same way as above, and then, charged into a well. After incubated at 37° C. for 15 minutes, X-ray film was arranged under the plate, followed by exposing for one hour in a dark place. As a result, it has been found that alkaline phosphatase was synthesized in an amount of 10 to 100 femtomoles based on 10 µL of the capsule concentrate.

What is claimed is:

1. A method for producing a reaction capsule comprising: concurrently extruding a plurality of concentric layers from a plurality of nozzles into a cooling solution, wherein an inner nozzle extrudes an aqueous reaction mixture comprising components required for synthesizing a polynucleotide or a polypeplide; an intermediate nozzle extrudes a viscous fluid that is not miscible with water; and an outer nozzle extrudes an encapsulating polymer layer formed of polysaccharide, protein, or a mixture thereof to form a reaction capsule; and isolating the reaction capsule from the cooling solution, wherein the flow rate from the nozzles is controlled to produce a capsule having an approximate diameter of 0.1 to 10.0 mm.

2. The method of claim 1, wherein the flow rate is controlled to produce a capsule having an approximate diameter of 3 mm.

3. A reaction capsule produced by a process comprising: concurrently extruding, a plurality of concentric layers from a plurality of nozzles into a cooling solution, wherein an inner nozzle extrudes an aqueous reaction mixture comprising components required for synthesizing a polynucleotide or a polypeptide; an intermediate nozzle extrudes a viscous fluid that is not miscible with water; and an outer nozzle extrudes an encapsulating polymer layer formed of polysaccharide, protein, or a mixture thereof; and isolating from the cooling solution a reaction capsule, wherein the flow rate from the nozzles is controlled to produce a capsule having an approximate diameter of 0.1 to 10.0 mm.

4. A reaction capsule for producing a nucleic acid or amino acid polymer therein, comprising:

a core comprising an aqueous reaction mixture for producing a nucleic acid or amino acid polymer;

a polymer layer encapsulating the core, the polymer layer formed of polysaccharide, protein, or a mixture thereof; and an intermediate layer comprising a viscous fluid disposed between the core and the encapsulating polymer layer, wherein said capsule has a diameter of about 0.01 to about 10.0 mm.

5. The reaction capsule of claim 4, wherein said aqueous mixture comprises components for polymerase chain reaction (PCR).

6. The reaction capsule of claim 4, wherein said aqueous mixture comprises a reverse transcriptase.

7. The reaction capsule of claim 4, wherein said core comprises components for cell free translation.

8. The reaction capsule of claim 4, wherein said core comprises one or more RNA or DNA polymerase.

9. The reaction capsule of claim 4, wherein said core comprises components for nucleic acid transcription and cell free translation.

10. The reaction capsule of claim 4, wherein said polymer layer comprises curdlan, agarose, guaran gum, pectin, sodium alginate, or mixtures thereof.

11. The reaction capsule of claim 10, wherein said polymer layer comprises curdlan, agarose, or a mixture thereof.

12. The reaction capsule of claim 11, wherein said polymer layer comprises a mixture of curdlan and agarose having an approximate weight ratio of 1:1.

13. The reaction capsule of claim 4, wherein said polymer layer comprises gelatin, albumin, casein, or a mixture thereof.

14. The reaction capsule of claim 4, wherein said polymer layer further comprises a gelling agent.

15. The reaction capsule of claim 14, wherein said gelling agent is calcium chloride, calcium lactate, manganese chloride, aluminum chloride, or mixtures thereof.

16. The reaction capsule of claim 4, wherein said polymer layer further comprises a water-soluble polyol or water-soluble polyol derivative.

17. The reaction capsule of claim 16, wherein said water-soluble polyol or water-soluble polyol derivative is glycerin, polyglycerine, sorbitol, ethylene glycol, polyethylene glycol, propylene glycol, polypropylene glycol, ethylene oxide-propylene oxide copolymer, oligosaccharide, sugar ester, glyceride, sorbitan ester, or mixtures thereof.

18. The reaction capsule of claim 4, wherein said polymer layer comprises polysaccharide, protein, or mixture thereof in an amount of approximately 50–100% by weight of the total solids content.

19. The reaction capsule of claim 4, wherein said intermediate layer comprises a viscous liquid having a viscosity of 1,000 centipoise or less.

20. The reaction capsule of claim 4, wherein said intermediate layer comprises and emulsifier, an oil, a resin, or mixtures thereof.

21. The reaction capsule of claim 20, wherein said intermediate layer comprises a sucrose fatty acid ester, propylene glycol fatty acid ester, glycerin fatty acid ester, sorbitan fatty acid ester, lecithin, palm oil, silicone oil, liquid paraffin, dl-alpha-tocopherol, polybutylene, polybuten, silicone resin, vinyl acetate, or mixtures thereof.

22. The reaction capsule of claim 21, wherein said intermediate layer comprises a mixture of sucrose fatty acid ester and palm hydrogenated oil in a weight ratio of 1 to 4: 4 to 1.

23. The reaction capsule of claim 22, wherein said weight ratio is 4:1.

* * * * *